US006748944B1

(12) United States Patent
DellaVecchia et al.

(10) Patent No.: US 6,748,944 B1
(45) Date of Patent: Jun. 15, 2004

(54) ULTRASONIC DOSAGE DEVICE AND METHOD

(76) Inventors: Michael Anthony DellaVecchia, 846 Farragut Rd., Berwyn, PA (US) 19312-2005; Claude Pezzopane, 243 Hill Rd., Honeybrook, PA (US) 19344

( * ) Notice: Subject to any disclaimer, the term of this patent is extended or adjusted under 35 U.S.C. 154(b) by 0 days.

(21) Appl. No.: 09/564,080

(22) Filed: May 3, 2000

(51) Int. Cl.$^7$ ......................... A61M 11/00; B05B 17/06

(52) U.S. Cl. ............................ 128/200.16; 128/200.14; 128/200.21; 128/202.25

(58) Field of Search ....................... 128/200.14, 200.16, 128/202.25, 200.21, 203.12

(56) References Cited

U.S. PATENT DOCUMENTS 3,102,535 A 9/1963 Dailey
3,219,029 A 11/1965 Richards et al.
3,589,363 A 6/1971 Banko et al.
3,828,769 A 8/1974 Mettler
3,948,264 A * 4/1976 Wilke et al. ........... 128/203.15
4,188,952 A 2/1980 Loschilov et al.
4,294,407 A * 10/1981 Reichl et al. ............... 239/102
4,601,698 A 7/1986 Moulding, Jr.
4,609,368 A 9/1986 Dotson, Jr.
4,634,419 A 1/1987 Kreizman et al.
4,657,543 A 4/1987 Langer et al.
4,760,799 A 8/1988 Jackson et al.
4,877,989 A * 10/1989 Drews et al. ............... 310/323
5,134,993 A * 8/1992 van der Linden et al. ..................... 128/200.14
5,261,601 A * 11/1993 Ross et al. ............... 239/102.2
5,483,953 A * 1/1996 Cooper .................. 128/200.22
5,485,828 A * 1/1996 Hauser .................. 128/200.16
5,529,055 A * 6/1996 Gueret .................. 128/200.16
5,694,920 A * 12/1997 Abrams et al. ........ 128/200.16
5,740,794 A 4/1998 Smith et al.
5,743,250 A * 4/1998 Gonda et al. .......... 128/200.14
5,775,320 A 7/1998 Patton et al.
6,012,454 A * 1/2000 Hodson et al. ........ 128/203.15
6,026,809 A * 2/2000 Abrams et al. ........ 128/203.15
6,062,212 A * 5/2000 Davison et al. ........ 128/200.16

FOREIGN PATENT DOCUMENTS

WO WO-9419042 A1 * 9/1994

* cited by examiner

*Primary Examiner*—Weilun Lo
*Assistant Examiner*—Darwin Erezo
(74) *Attorney, Agent, or Firm*—Caesar, Rivise, Bernstein, Cohen & Pokotilow, Ltd.

(57) ABSTRACT

An ultrasonic dosage device having an enclosure for providing a medication in the form of a nebulized mist, including an energy source positioned within the enclosure and a vibration device with a switch for applying electrical energy from the energy source to the vibration device. An assembly is attached to the enclosure and has a membrane disposed between the vibration device and the medication for containing the medication and maintaining the medication in contact with the vibration device only by way of the membrane, whereby the membrane is vibrated and the medication is thereby converted into the mist by vibrations transmitted to the medication by way of the membrane when power is applied to the vibration device.

4 Claims, 8 Drawing Sheets

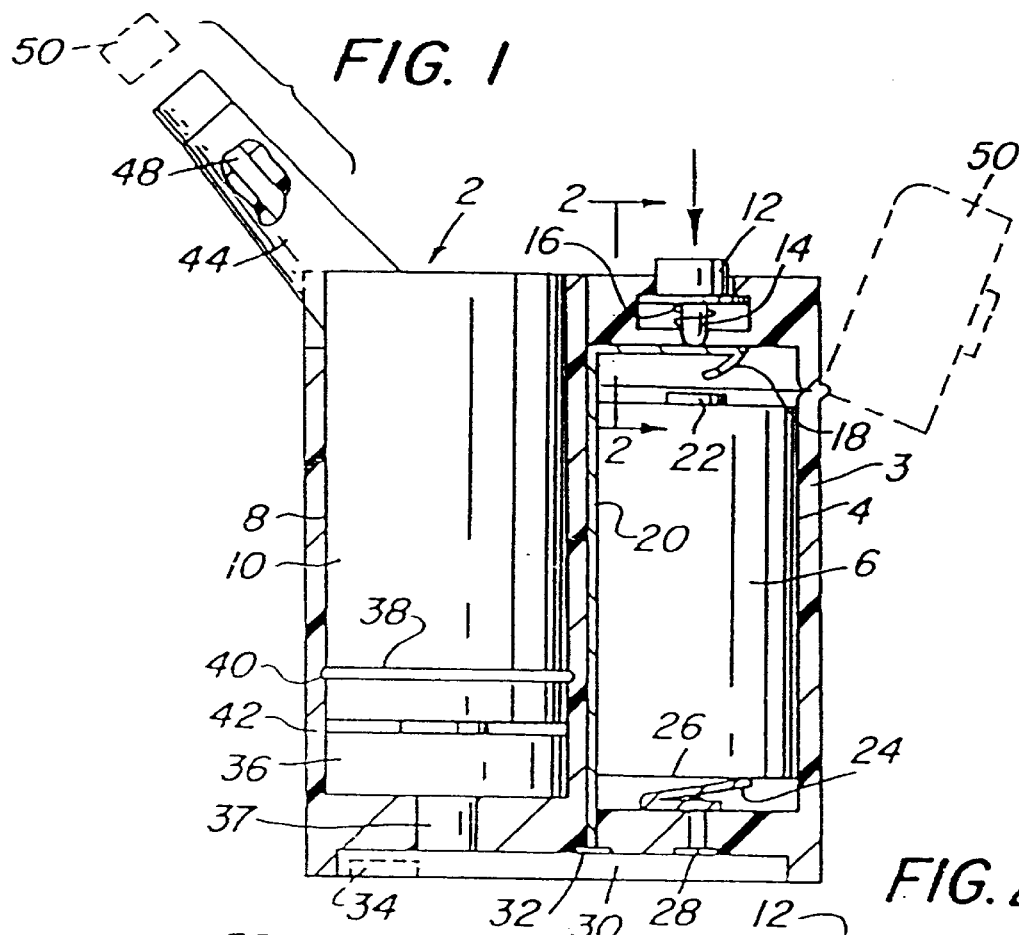
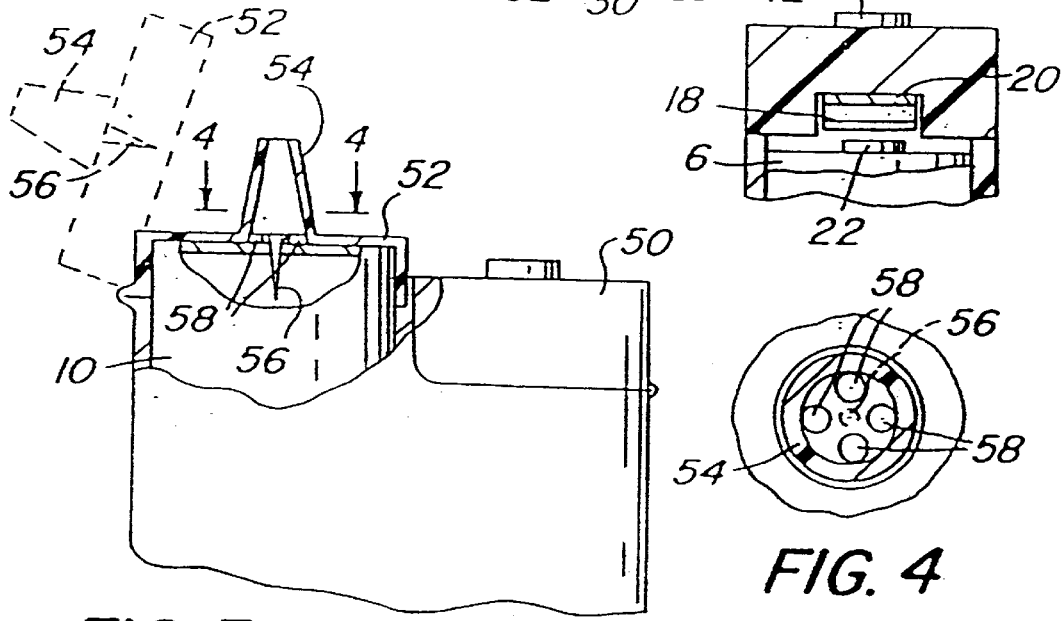

ULTRASONIC DOSAGE DEVICE AND METHOD

FIELD OF INVENTION

This invention relates generally to a dosage device and method for medicinal purposes, and more particularly, to a portable hand-held dosage device and cartridge which ultrasonically nebulizes a liquid or gel or powder or a combination of such for inhalation by the user.

BACKGROUND ART

Devices in prevalent use today use the standard devices for producing sprays. Either a pump is used or gases are used to create and eject the sprays under pressure. Squeeze containers, also used for sprays, create large droplets for injection into the mouth or nose.

For medicinal purposes, sprays are used which are inhaled either through the nose or the mouth and provide a delivery to the systemic system. The medicaments include water, decongestants, or other drugs for the treatment of colds, bronchitis, asthma, cutaneous diseases and the like. Furthermore, inhalation of medicaments into the lungs provides for a convenient and rapid way to apply treatment to other parts of the body, as well as to the breathing passages and lungs of the user.

With ultrasonic inhalation techniques it is known to get a more usable concentration of droplet size. Ultrasonic techniques can produce a larger percentage of the droplets having a useful size compared with the percentage that is commonly available for other types of pneumatic administration of the medication. The use of screens to control particle size is also known.

Various medicinal and medical devices are presently known which employ ultrasonic transducers. L. E. Dailey, TRANSDUCER DEVICE, U.S. Pat No. 3,102,535; Mettler, METHOD AND APPARATUS FOR ULTRASONIC TREATMENT OF LOWER TISSUES SIMULTANEOUS WITH HEATING OF SUBCUTANEOUS, OUTER MUSCLE AND LOWER TISSUES, U.S. Pat No. 3,828,769; and J. M. Richards, et al., REMOTE CONTROL MEDICAL THERAPY INSTRUMENT, U.S. Pat. No. 3,219,029 teach the use of ultrasound for physical therapy of muscles and tissues for various parts of the body.

An ultrasonic dosage device for direct inhalation of medicaments by the user or for application to other internal and external body areas. The device in the preferred embodiment has a rechargeable and/or replaceable storage battery which operates an ultrasonic transducer. A cartridge containing medicament is placed atop the ultrasonic transducer. The cartridge may be disposable and/or sterile or reusable or within itself contain the ultrasonic transducer. The ultrasonic energy created by the transducer converts the liquid, powder or gel medicament into a fine vapor or mist. A spout attached to the (disposable) cartridge may be placed into the mouth or nostrils, or natural, traumatic or surgical air passages of the user for inhalation of the vapor. Alternatively it may be placed against a body part such as the eye, membranes or integument. Alternatively, the spout may be hinged to the device and include a spike which punctures the top of the disposable cartridge to allow vapors to escape for inhalation by the user.

Ultrasound techniques are also used to increase the efficiency of surgical cutting tips in Kriezman, et al., ANGULATED ULTRASONIC SURGICAL HANDPIECES AND METHOD FOR THEIR PRODUCTION, U.S. Pat No. 4,634,419; Dotson, Jr., PNEUMATIC ULTRASONIC SURGICAL HANDPIECE, U.S. Pat. No. 4,609,368; Loschilov, et al., SURGICAL INSTRUMENT FOR ULTRASONIC SEPARATION OF BIOLOGICAL TISSUE, U.S. Pat No. 4,188,952; and Banko, et al., MATERIAL REMOVAL APPARATUS AND METHOD EMPLOYING HIGH FREQUENCY VIBRATIONS, U.S. Pat No. 3,589,363.

Other usage of ultrasonic equipment in medical practice consist of vibration of medicinal fluids as taught by Moulding, Jr., METHOD OF AND INSTRUMENT FOR INJECTING A FLUID INTO A UTERINE CAVITY AND FOR DISPENSING THE FLUID INTO THE FALLOPIAN TUBES, U.S. Pat No. 4,601,698; and Crowson, SONIC TEETH-CLEANING APPARATUS AND METHOD, U.S. Pat. No. 4,760,799.

Still another use of ultrasonic devices in the medical field is to control the delivery of biologically active substances from a polymer matrix as taught by Langer, et al., A ULTRASONICALLY MODULATED POLYMERIC DEVICES FOR DELIVERING COMPOSITIONS, U.S. Pat No. 4,657,543.

Although the above devices and techniques may be suitable for the purpose for which they are intended, none of these devices or techniques use ultrasonic techniques for the purpose of vaporizing a liquid, powder, or gel medicament for direct inhalation by the user. Ultrasonic vaporization of medicaments provide a very fine mist for more efficient and greater absorption by the tissues and lungs of the user.

OBJECTS OF THE INVENTION

It is the general object of the instant invention to provide an ultrasonic dosage device, container and method for the application of medicaments which overcome the shortcomings of existing devices.

It is another object of the instant invention to provide an ultrasonic dosage device, container and method which converts and applies medicaments in liquid gel or powdered form to vapor for application by the user.

It is yet another object of the instant invention to provide an ultrasonic dosage device, container and method for the inhalation of medicaments which is portable and hand-held.

It is still yet another object of the instant invention to provide an ultrasonic dosage device, container and method which uses a transducer powered by a rechargeable or replaceable battery or adaptor to provide ultrasonic energy to convert a (liquid), powder or gel medicament to a vapor.

It is a further object of the instant invention to provide an ultrasonic dosage device and method to be used with a disposable and/or sterile (or reusable) cartridge containing a medicament, which can also be dispersed and delivered in a unit dose.

It is a further object of the instant invention to provide an ultrasonic dosing device and method which can provide a vaporized medicament with a passively or negatively charged particle.

It is a further object to provide electrostatic control of the method of suspension and emission.

It is yet a further object of the instant invention to provide an ultrasonic dosage device with a spout for inhalation attached to a disposable cartridge containing a liquid medicament.

It is still yet a further object of this invention to provide an ultrasonic dosage device, or container and method with a hinged spout for application of medicaments and a spike to pierce a disposable cartridge containing a medicament to be vaporized by the device for application.

SUMMARY OF INVENTION

These and other objects of the instant invention are achieved by providing a device and a method in which a cartridge of a medicament in liquid, gel or powder form is transformed into vapor form for inhalation by the user through the use of an ultrasonic transducer or acoustically transmissible barrier. The device comprises a rechargeable storage battery, a printed circuit board, and a transducer which is powered by a rechargeable battery or adaptor. A disposable cartridge is inserted into the device so that it abuts the transducer. When power from the battery is applied to the transducer, the liquid in the cartridge is ultrasonically vibrated to convert the liquid into a vapor for direct application to the user. The medicament is provided within a sealed assembly placed in vibrational contact with the transducer. The sealed assembly can be sterile. The vapor particles can be electrostatically charged prior to application to the user. A push button, protected by a hinged cover, is used to apply power to the transducer when desired. Alternately the device can be initiated by a change in lung pressure, chest expansion, pneumography and electrocardiography. The printed circuit board provides power connections between the rechargeable battery and the transducer, and a regulator for regulating the power used to recharge the battery. The printed board also contains a female socket for connection to a battery recharger. In one alternate approach, a spout is connected directly to the disposable cartridge. After or during the substance is or has been vaporized, a cover is removed from the end of the spout for direct inhalation by the user.

In an alternative approach, a spout with a spike is hinged to the device. After the disposable cartridge is placed within the device, the hinged cover is closed and the spike pierces the cartridge. After ultrasonic vaporization of the liquid in the cartridge, the spout is placed directly into the mouth of the user, or into the nostrils of the user, for direct inhalation of the vapors or against body parts such as the integument. Various ways to securely lock the disposable cartridge against the transducer during ultrasonic vibration are included."

BRIEF DESCRIPTION OF THE DRAWINGS

Other objects have many of the attendant advantages of this invention will be readily appreciated when the same becomes better understood by reference to the following detailed description when considered in connection with the accompanying drawing wherein:

FIG. 1 is a sectional view of the device of the instant invention.

FIG. 2 is a sectional view showing the push button and/or initiating mechanism for the application of power to the transducer of the device taken along the line 2—2 of FIG. 1.

FIG. 3 is a side view, partially in section, of the device of the instant invention, showing an alternate embodiment of the spout portion of the device for inhalation by the user.

FIG. 4 is a sectional view of the base of the spout of FIG. 3 showing the passages through which the vapor flows when inhaled by the user, taken along the line 4—4 of FIG. 3.

Figure 5:
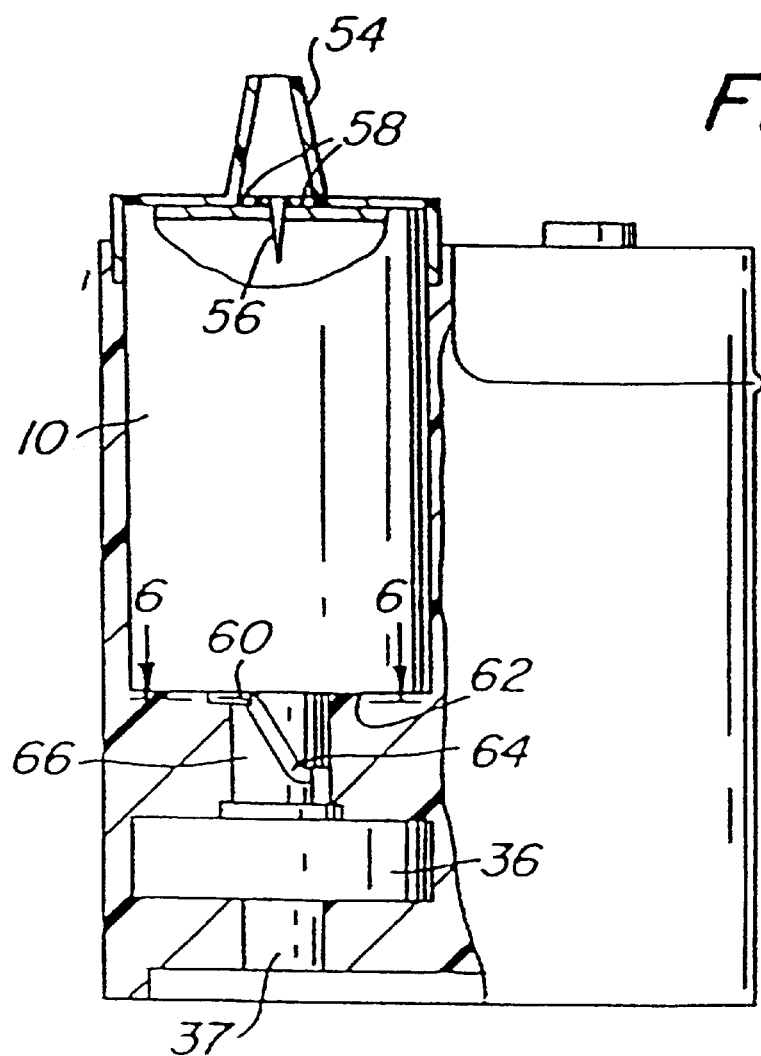
FIG. 5 is a side view of the device of the instant invention, which describes an alternate method for securing the disposable cartridge of liquid medicament against the ultrasonic transducer.

FIG. 15 is a graphical representation of the droplet distribution of materials nebulized, charged, and expelled by the device of the instant invention.

FIG. 16 is a graphical representation of the droplet distribution of materials nebulized, charged, and expelled by the device of the instant invention.

DESCRIPTION OF THE PREFERRED EMBODIMENT OF THE INVENTION

Referring now, in greater detail, to the various figures of the drawing wherein like reference characters refer to like parts, there is shown in FIG. 1 a embodiment of the ultrasonic dosage device and method of the present invention. The enclosure 3 of the ultrasonic dosage device includes a battery chamber 4 in which a storage battery 6 or other power supply can be located. The enclosure 3 also includes a cartridge chamber 8 into which a disposable cartridge may be placed. The dosage device of this embodiment of the invention is quite light in weight, having a weight of approximately one pound. However, the present invention in other embodiments also contemplates a heavier device relying upon a plug-in (AC) power source. Such heavier device may still be portable.

The ultrasonic device of the present invention includes a push button 12 for applying battery power to the device. The push button 12 is connected to a shaft 14. A spring 16 disposed about the shaft 14 keeps the push button 12 in its steady state position when the push button 12 is not operated. Depressing the push button 12 causes a bent member 18 attached to conductor lead 20 to make contact with the positive pole connector 22 of the rechargeable storage battery 6. The initiator could also be a computer, such as a microprocessor or a transducer monitoring a parameter such as the respiratory cycle or chest expansion.

A conductor spring 24 is connected at one end to the negative pole 26 of the rechargeable storage battery 6. The other end of the conductor spring 24 is connected to a terminal 28 which is in turn connected to a conductor in a printed circuit board 30. The distal end of the conductor lead 20 is connected to terminal 32 of the printed circuit board 30. As shown with dashed lines, female socket 34 is located within the printed circuit board 30. The female socket 34 may be connected to the output of a battery recharger, to recharge the rechargeable storage battery 6 when not in use. The printed circuit board 30 also includes a regulator (not shown) and connections to the storage battery 6 to provide a recharging input to the storage battery 6 when the output of a battery recharger is connected to the female socket 34.

Figure 10:
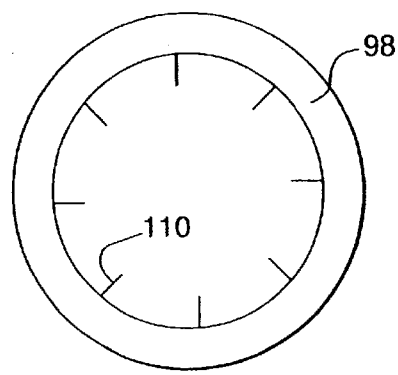
FIG. 10 shows an electrostatic ring with ion emitters disposed thereon suitable for use in the device of the instant invention.

A circumferential ring 38 on the disposable cartridge 10 is locked into place when it meshes with a circular indentation 40 in the chamber wall 42. When thus positioned, the disposable cartridge 10 rests securely upon an ultrasonic transducer 36 which is connected to the printed circuit board 30 through connections within conductor passage 37, as can be seen in FIG. 10. The ultrasonic transducer 36 can be a Piezo ceramic or magnetostrictive type of transducer. Furthermore, the ultrasonic transducer 36 can have a disk type configuration as well as a center bolt configuration or any other type of ultrasonic transducer configuration known in the art.

The frequency of the vibration of the ultrasonic disc 36 can be used to control the size of the droplets expelled by the device of the present invention. To some extent the frequency of the ultrasonic transducer 36 can be controlled by the frequency of the excitation energy applied to it. However, since the ultrasonic device 36 is a resonant device it has a limited range of frequencies. Therefore, ultrasonic devices 36 of varying sizes are required to obtain a large range of frequencies and, thereby, a large range of particle sizes.

Figure 7:
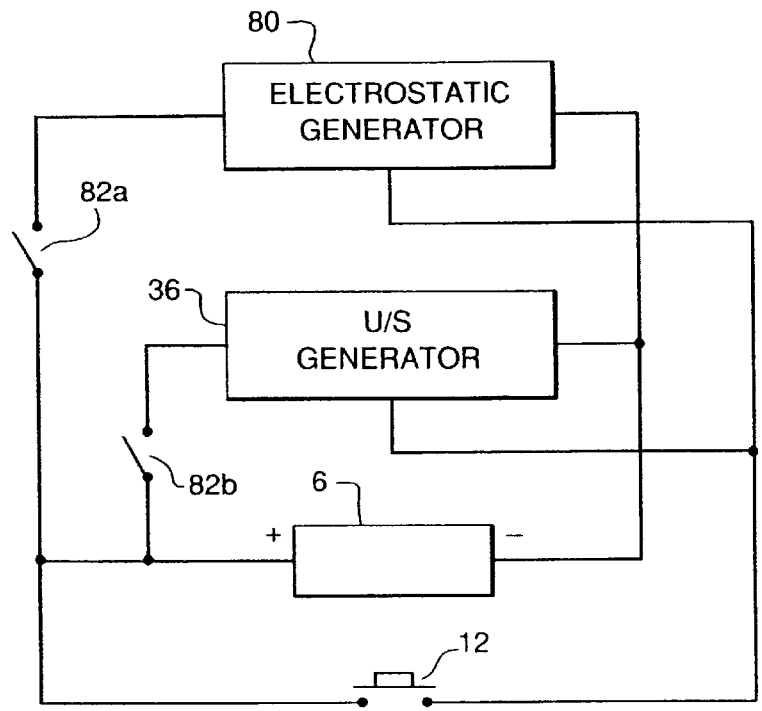
FIG. 7 shows an electrical circuit suitable for use within the device of the instant invention for nebulizing and charging materials.
Figure 8:
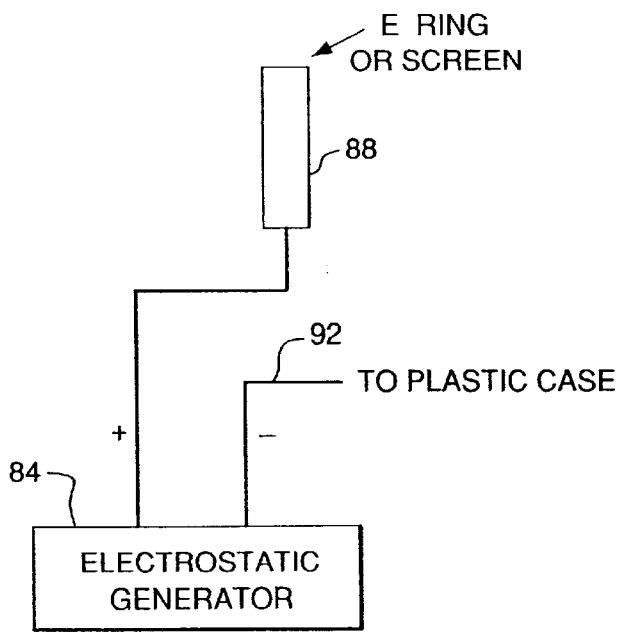
FIG. 8 shows an electrical circuit suitable for use within the device of the instant invention for charging materials.

Referring now to FIGS. 7,8, there are shown electric circuits suitable for use in the device of the present invention. When push button 12 is pressed power is applied from the battery 6 to the ultrasonic transducer 36. The ultrasonic energy produced thereby is transmitted to the disposable cartridge which vaporizes the medicament liquid therein. Spout 44 is connected to the top of disposable cartridge 10 and is covered by a cover 50 when not in use. After vaporization of the medicament in the disposable cartridge the vapor mixes with air and flows through a passage 48 and into the mouth or nostrils of the user for inhalation of a mist into the lungs. The minute drops of the therapeutic mist created by the dosage device of the present invention are of an extremely fine particle size, being as small as about one micron in particle size or smaller, as compared with particles of approximately thirty microns in size that are created by mechanical dosage devices.

In addition to energy from battery 6 being applied to the ultrasonic generator 36 when the switch 12 is depressed, energy from the battery 6 is also applied to an electrostatic generator 80 by depressing switch 12. The operations of the electrostatic generator 80 are described in detail below. Additionally, switches 82a,b are disposed between the battery 6 and electrostatic generator 80 and ultrasonic generator 36. Switches 82a,b permit the selective operation of the electrostatic generator 80 and the ultrasonic generator 36 whereby either generator 80, 36 can be operated without operating the other.

FIG. 2 is a sectional view showing the push button 12, the conductor lead 20, and the bent member 18, taken along the line 2—2 of FIG. 1. As explained previously, depressing the push button 12 causes the bent member 18 to contact the positive pole connector 22 to allow power to flow from the rechargeable storage battery 6. The power flows through the printed circuit board 30 and into the transducer 36 and electrostatic generator 80. It is understood that conventional circuitry on printed circuit board 30 provides high frequency energy for application to transducer 36 in response to the energy from battery 6.

An alternate embodiment of the spout arrangement in FIG. 1 is shown in FIG. 3. As may be seen in FIG. 3, hinged spout assembly 52 comprises spout 54 and spike 56. When not in use, hinged spout assembly 52 is rotated to cover cartridge chamber 8. For use, the hinged mouth piece assembly 52 is rotated counterclockwise about its hinge to open and provide access to cartridge chamber 8, as shown by the dashed lines in FIG. 3. After the disposable cartridge 10 has been placed into the cartridge chamber 8, the hinged spout assembly 52 is rotated clockwise to cover the disposable cartridge 10, so that the spike 56 pierces the top of the disposable cartridge 10. This allows the vapor in the disposable cartridge 10 to escape into the spout 54 for inhalation through the users mouth or nostrils. While the ultrasonic dosage device of the present invention is primarily intended for use as an inhalant device, it is also suitable for application of medicaments to the integument of the user.

FIG. 4 shows a sectional view, taken along the line 4—4 of FIG. 3. As may be seen in FIG. 4, the vapor from the disposable cartridge 10 is free to flow through the passages 58 into the spout 54 for inhalation by the user.

Figure 6:
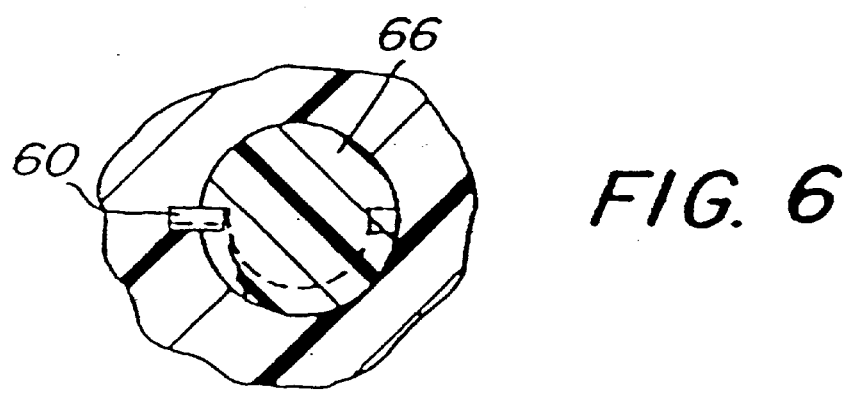
FIG. 6 is a sectional view of the securing device of the system of the present invention taken along the lines 6—6 of FIG. 5.

An alternate embodiment for locking the disposable cartridge into position atop the ultrasonic transducer 36 is shown in FIG. 5. In this embodiment, the disposable cartridge 10 is positioned by rotating the disposable cartridge so that a pin 60 attached to a bottom wall 62 of the disposable cartridge 10 is caused to ride a threaded portion 64 of bayonet mount 66. A sectional view of the bayonet mount, taken along the line 6—6 is shown in FIG. 6.

The device of the present invention may be fabricated using inexpensive commercially available parts. For example, the storage battery 6 can be a Sanyo Cadnica sub-C size battery and the ultrasonic transducer can be a TDK-TU-26B device. Other parts are made of a plastic, like vinyl plastic. Additionally, the storage battery 6 can be a battery other than a nicad battery. Furthermore, an AC to DC converter can be used to energize the ultrasonic dosage device of the present invention.

As described above, the present invention provides a portable handheld device and method for ultrasonically vaporizing a liquid medicament for treatment of conditions of the air passages and lungs of the user. However, the present invention is also capable of being used for delivery of medicines as well as moisture to other areas, such as the skin or the eyes. Furthermore, the device may be used to apply medicaments or drugs to various parts of the body through absorption through the lungs and into the blood stream of the user.

Figure 9:
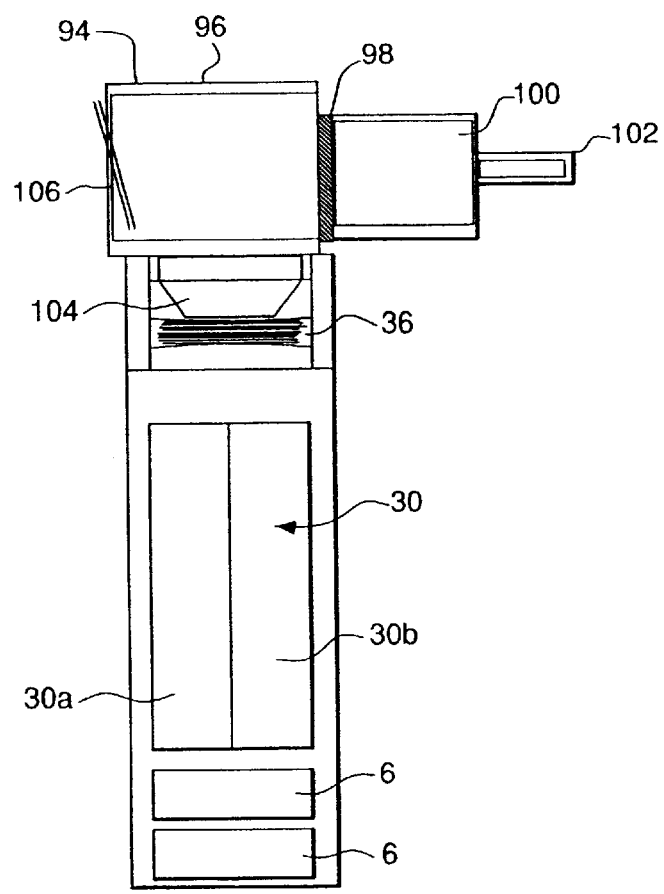
FIG. 9 is a sectional view of a cartridge showing an incorporated ultrasonic membrane and an electrostatic ring for charging the vaporized particles.

Referring now to FIGS. 9,10, another variation of the invention is shown wherein the variation set forth can be provided as a portable device or as a non-portable device. The ultrasonic inhalant device of FIG. 9 provides a very fine vaporization mist that enhances the absorption of the medicament into the tissues and lungs of the user as previously described. Printed circuit board 30 includes circuitry for generating ultrasonic frequency electrical signals for application to the ultrasonic disk.

Additionally, printed circuit board 30 includes circuitry for generating an electrostatic voltage and applying an electrostatic charge to the particles created by ultrasonic disk 36. Such electrostatically charged particles remain in aerosolized suspension substantially longer than uncharged suspension particles. The electrostatic portion of the circuitry 30 is designated as circuitry 30b and the mouth of the user is grounded to circuitry 30b when the mouthpiece 102 is applied to the mouth of the user.

It is known to those skilled in the art that there are large polar groups on the surfactants of the mucous lining of the respiratory tract or lung parenchyma. The charge on the charged particles and the mucous lining allows the charged particles to remain in suspension longer and to thereby invade the respiratory areas deeper. It also causes the particles that come in contact with the membranes to adhere to the membranes more readily thereby causing greater adherence to the surface of interest to help reduce dosage cost. Furthermore, it is believed that many sores within the lungs have a charge differing from the charge of their surrounding tissue. Thus, applying an appropriate level and polarity of charge to the particles can assist in concentrating the particles on the sores. For example, if the sores are more positive, then a negative charge on the particles can concentrate the particles on the sores.

The ultrasonic dosage device of FIG. 9 includes a disposable sealed medication assembly 94. The disposable sealed medication assembly 94 is adapted to be detachably secured to the ultrasonic dosage device in order to permit the medication to be applied to the user and removed from the ultrasonic dosage device thereafter. When it is purchased by the user the disposable sealed medication assembly 94 is a presealed unit including therein the medication to be administered to the user. The medication falls into a chamber formed by a membrane diaphragm 104 and resides therein when the ultrasonic dosage device is upright. The membrane diaphragm 104 can be a foil.

The disposable sealed medication assembly 94 also includes nebulization chamber 96 above the chamber formed by diaphragm 104. The nebulization chamber 96 is in fluid communication with the chamber formed by diaphragm 104. The nebulization chamber 96 is also in fluid communication with a charged chamber 100. The charged chamber 100 has an outlet mouthpiece 102. The contents of the entire sealed volume of medication assembly 94 is sterile in the preferred embodiment of the invention.

When the disposable sealed medication assembly 94 is secured to the dosage device, the surface of diaphragm 104 rests against ultrasonic disc 36. When the ultrasonic generator circuit 38 is energized and the ultrasonic disc 36 vibrates, the vibrations are mechanically coupled to the medicinal material within diaphragm 104 because of the physical contact therebetween. The invention thereby eliminates the loss of sterility caused by pouring medication into a container for nebulization or piercing a container when applying the medication to a user. The nebulized medication formed thereby rises into the nebulization chamber 96 and is expelled therefrom into the charged chamber 100. An air inlet 106 can be provided on the wall of nebulization chamber 96 opposite the opening into the charged chamber 100 in order to assist in this expelling motion and mix the medication with air.

An electrostatic ring 98 is disposed around the charged chamber 100 substantially close to the nebulization chamber 96. When the nebulized particles are expelled from nebulization chamber 96 into the charged chamber 100 the particles are provided with an electrostatic charge if the electrostatic ring 98 is energized.

The disposable sealed medication assembly 94, in the preferred embodiment of the invention, can contain a single sterile dose of the medication to be applied to the user. Thus, after a single use the user can detach the disposable sealed medication assembly 94 from the inhalation device and discard the assembly 94. A new disposable sealed medication assembly 94 can be used for the administration of the next dose by detachably securing it to the inhalation device. The mouthpiece 102 and the air inlet 106 of a medication assembly 94 can be covered, for example with plastic covers, in order to preserve the sterility of the medication assembly 94.

The electrostatic ring 98 is provided with a plurality of inwardly extending emitters 110 for more efficiently charging the particles passing therethrough. In an alternate embodiment of the invention, the electrostatic ring 98 can be disposed around or above the chamber formed by the diaphragm 104. It can be disposed at different locations along the chambers of the sealed medication assembly 94 or even along the mouthpiece 102. It can be disposed at any location that permits the atomized particles to pass therethrough and be electrostatically charged. However, it is believed to be most efficient to dispose the electrostatic ring 98 on the charged chamber 100 near the nebulization chamber 96 as shown. The electrostatic ring 98 of the invention works by inductive charging by electrostatic circuitry 30b in a manner well known to those skilled in the art.

The nebulized particles of the mist provided by the dosage device of the invention can be electrostatically charged by contact charging, which is physically adaptable to the present invention. However, it is believed that this would be not the optimum method. An induction method, however, allows for the particles to go through an electrostatically charged field and upon their exit be negatively or positively charged. The charge applied to the particles remains in effect until it is dissipated through the atmosphere at a slow exponential rate of decay.

Figure 11:
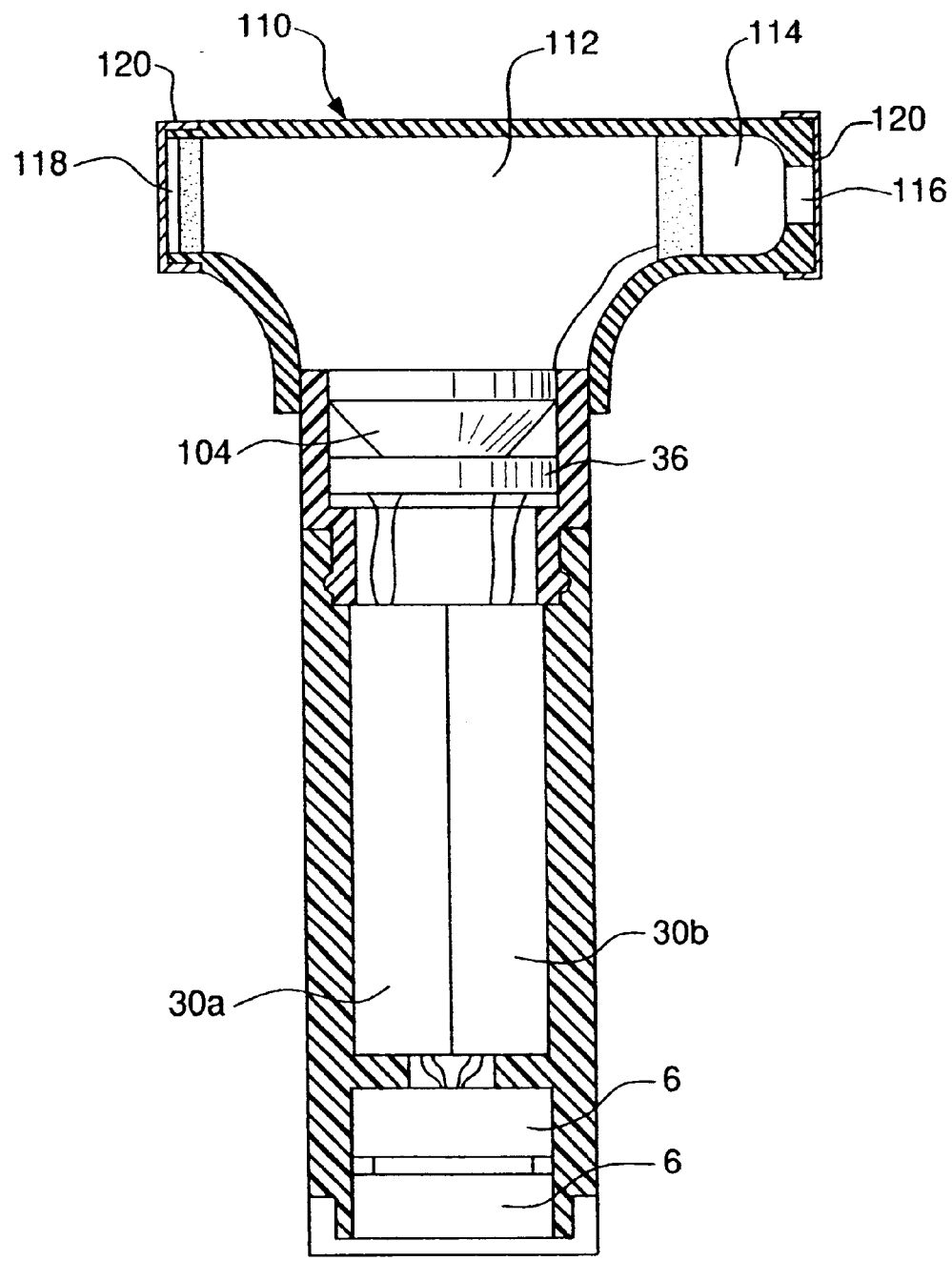
FIG. 11 is a sectional view of the device of the invention, which describes an alternate method for securing the disposable cartridge of medicament with protective packaging and incorporating an ultrasonic membrane or transducer and an electrostatic grid.
Figure 12:
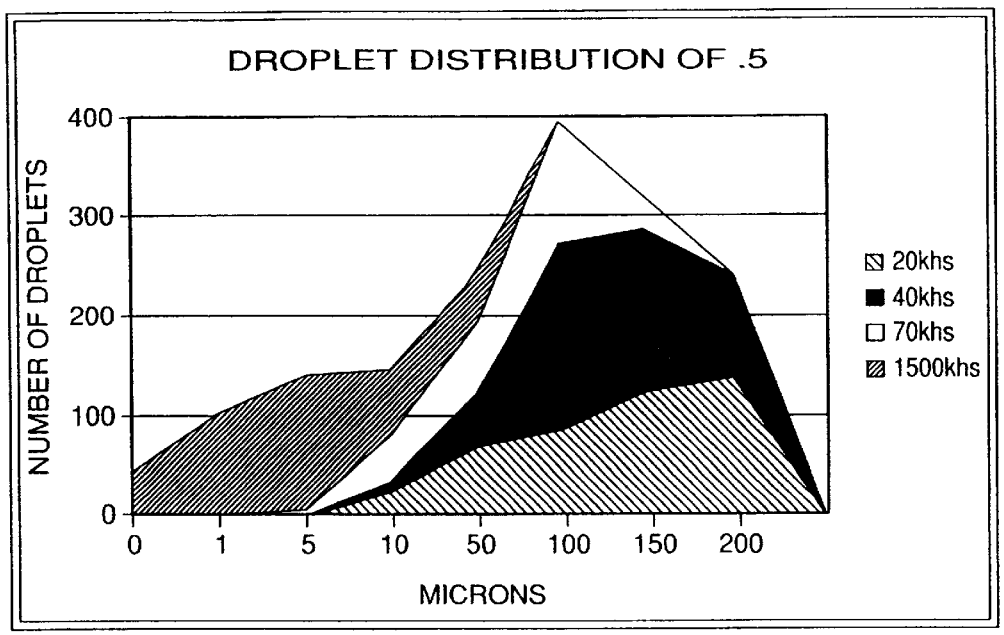
FIG. 12 is a graphical representation of the droplet distribution of materials nebulized, charged, and expelled by the device of the instant invention.
Figure 13:
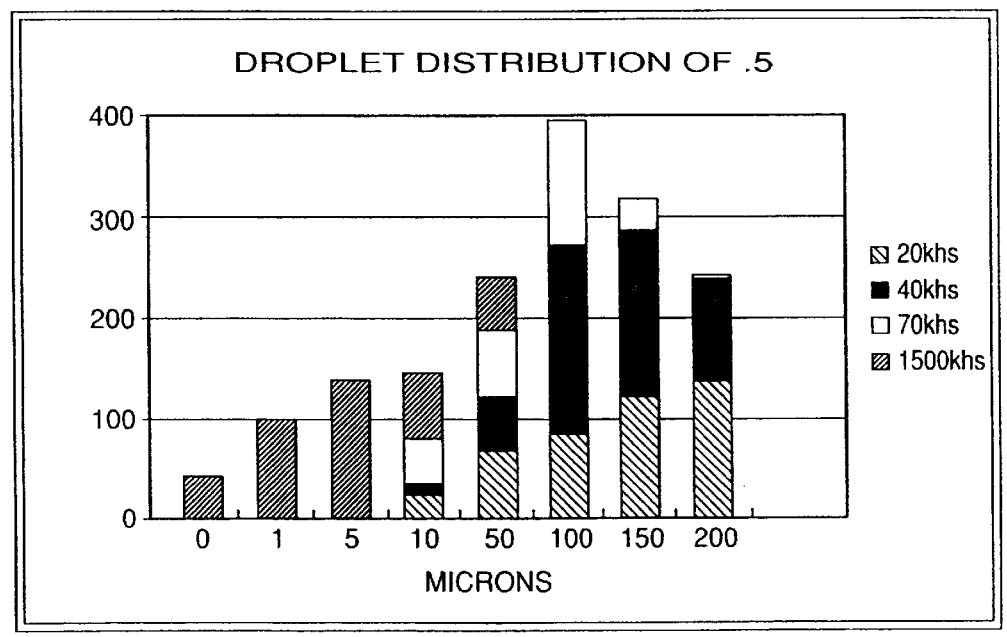
FIG. 13 is a graphical representation of the droplet distribution of materials nebulized, charged, and expelled by the device of the instant invention.
Figure 14:
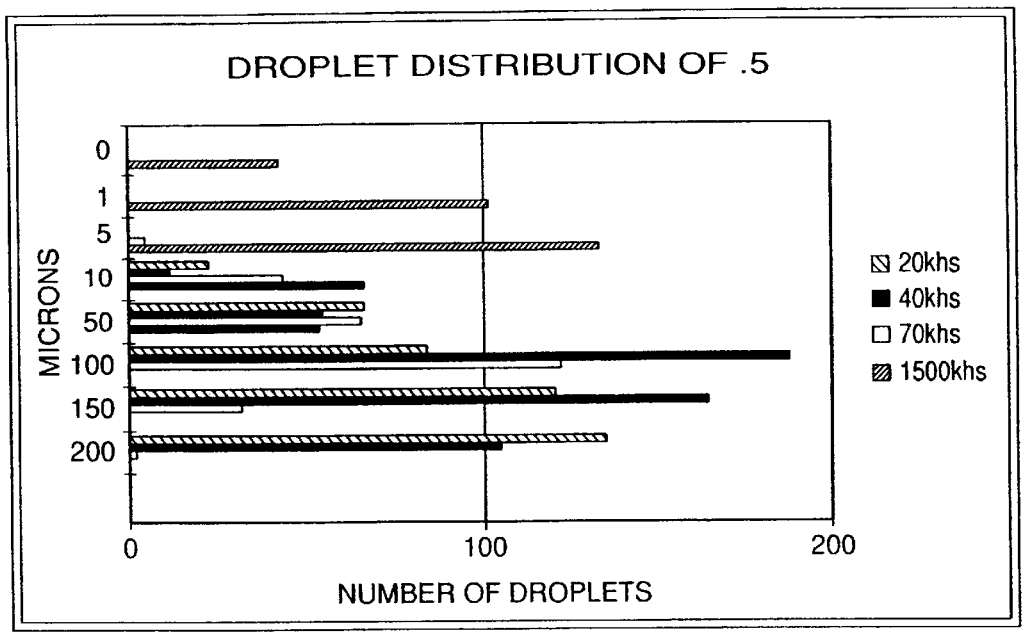
FIG. 14 is a graphical representation of the droplet distribution of materials nebulized, charged, and expelled by the device of the instant invention.
Figure 15:
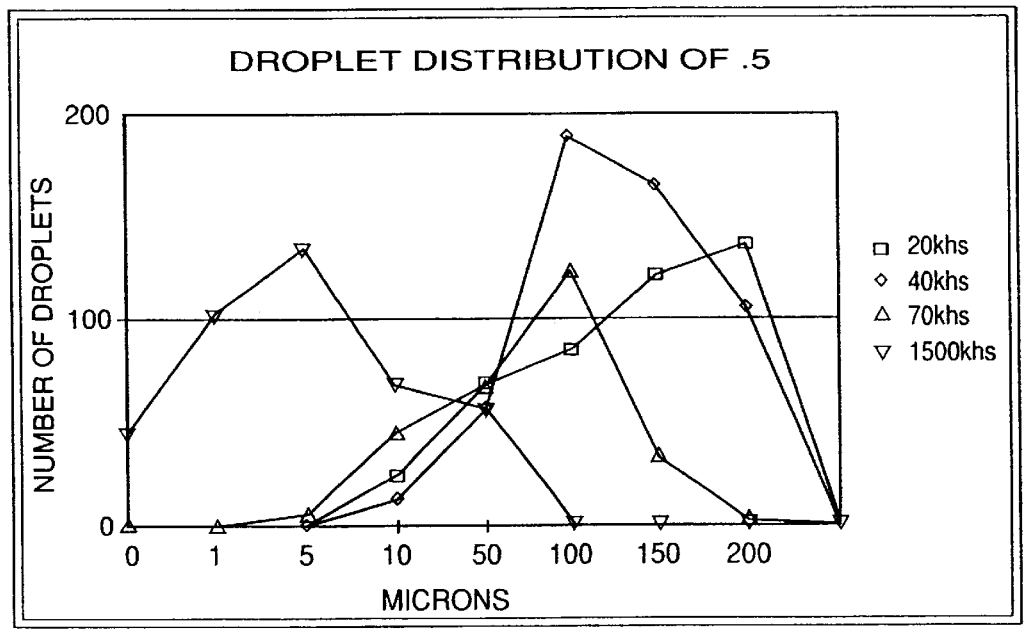
Figure 16:
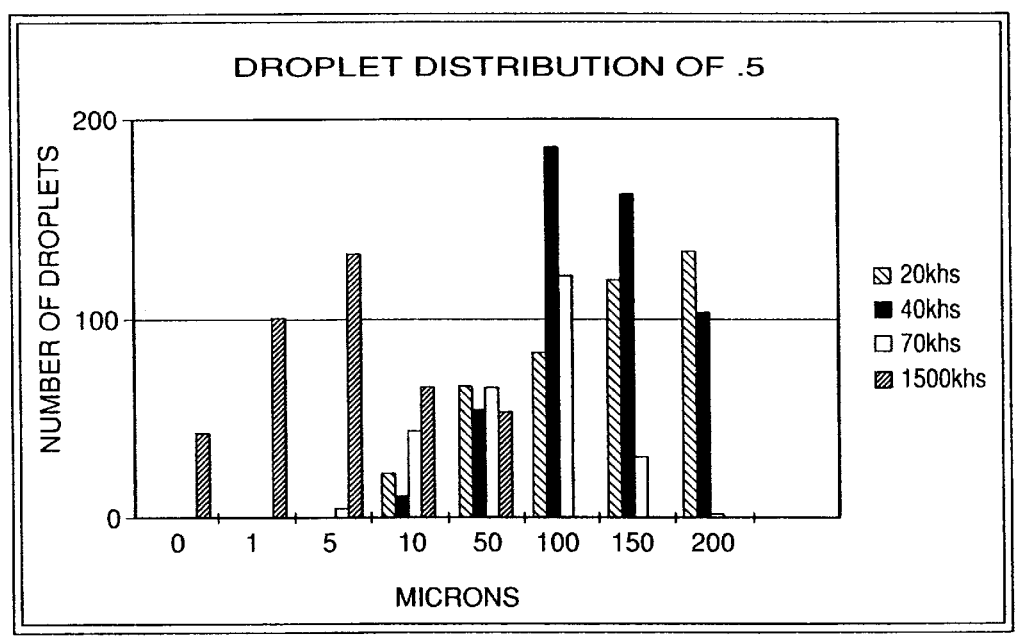

Referring now to FIG. 11, there is shown an alternate embodiment of the inhalation device of the invention. The embodiment of FIG. 11 includes an enclosure containing batteries 6, circuitry 30a,b and an ultrasonic transducer 36 as previously described. Additionally, a disposable sealed medication assembly 110 is provided. In the preferred embodiment the disposable sealed medication assembly 110 is sterile as previously described with respect to sealed medication assembly 94. The chamber formed by a diaphragm 104 for containing the medication to be applied to the user is disposed against the surface of the ultrasonic transducer 36 and is provided with an upper opening into a nebulization chamber 112. The nebulization chamber 112 communicates with a charged chamber 114 for charging particles that are expelled from the nebulization chamber 112 and into the charged chamber 114. The charged particles are expelled through mouthpiece 116 with assistance from air drawn into the sealed medication assembly 110 by way of air vent 118. Plastic covers 120 are provided to cover air intake 118 and mouth piece 116 in order to preserve the sterility of the medication sealingly contained within the disposable sealed medication assembly 110.

Referring now to FIGS. 12–16, there are shown graphical representations of the droplet size distribution of the particles produced by the electrostatic dosage device of the present invention. The dosage distribution is demonstrated for ultrasonic device 36 frequencies of twenty kilohertz, forty kilohertz, seventy kilohertz and 1,500 kilohertz. In addition to the frequency of vibration, the surface area in contact between ultrasonic device 36 and diaphragm 104 can determine the droplet distribution. The measurements of the number of droplets of the varying sizes are made using conventional laser scattering methods of measurement. However, it will be understood by those skilled in the art that a frequency of 1,500 kilohertz provided the greatest number of droplets in the range of zero to ten microns.

Since smaller droplet sizes result in longer suspension of the medication and therefore more opportunity for the droplets to reach into smaller passage ways of the lungs. Additionally, droplets of this size are more readily absorbed by the bronchial tubes. Therefore, droplets between zero and ten microns are preferred and droplets between zero and five microns are more preferred. Thus, the frequency 1,500 kilohertz is used in the preferred embodiment of the invention.

Without further elaboration, the foregoing will so fully illustrate the invention that others may, by applying current or future knowledge, readily adapt the same for use under various conditions of service.

We claim:

1. An ultrasonic dosage device having an enclosure for a medication in the form of a nebulized mist, said dosage device comprising;
   an energy source positioned within said enclosure;
   a vibration device with a switch for applying electrical energy from said energy source to said vibration device;
   an assembly attached to said enclosure, said assembly including;
   a nebulization chamber;
   an air inlet and a mouthpiece to provide an air path for permitting air to enter said assembly by way of said air inlet, pass through said nebulization chamber and exit said assembly by way of said mouthpiece;
   sterile inner assembly surfaces and non sterile outer assembly surfaces;
   an assembly membrane separate from said vibration device and from said enclosure until detachably securing the assembly to the enclosure;
   said membrane being integral with said nebulization chamber and disposed between said vibration device and said medication, and against said vibration device, for containing said medication until attaching said assembly to said enclosure and maintaining said medication in contact with said vibration device only by way of said assembly membrane;
   said membrane forming a chamber for permitting said medication to fall into said chamber and reside therein when said assembly is in a dosage administering position;
   said assembly having a removable assembly cover for providing sterility of said non sterile outer assembly surfaces until removing said assembly cover and detachably securing said assembly to said enclosure;
   said assembly membrane being vibrated by said vibration device in order to transmit vibrations from said vibration device directly to said medication and through said medication in order to convert said medication into said mist by said vibrations transmitted through said medication by way of said assembly membrane when power is applied to said vibration device wherein;
   said mist entering said air path through said nebulization chamber and coming in contact only with said sterile inner assembly and independent of contact with said non-sterile outer surfaces until exiting said assembly.

2. The device of claim 1, further comprising an electrostatic device for applying an electrostatic charge to medication particles forming said mist.

3. The device of claim 2, wherein said electrostatic device surrounds a region of said ultrasonic dosage device.

4. The device of claim 3, wherein said electrostatic device comprises a ring and said particles are changed while passing through a region defined by said ring.

* * * * *